United States Patent [19]
Ion

[11] 3,993,045
[45] Nov. 23, 1976

[54] TUBULAR MEASURING MEDICAL INSTRUMENTS

[76] Inventor: Elizabeth Edwinia Ion, 3902 Roseland, Houston, Tex. 77006

[22] Filed: Nov. 10, 1975

[21] Appl. No.: 630,324

[52] U.S. Cl. .................................... 128/2 S; 3/1; 33/174 D; 33/178 B; 128/303 R
[51] Int. Cl.² .......................................... A61B 5/10
[58] Field of Search ......... 128/1 R, 2 R, 2 S, 303 R; 33/174 D, 174 A, 174 N, 178 R, 178 B, 178 D, 178 F; 3/1.4; D52/6 A; D83/12 R

[56] References Cited
UNITED STATES PATENTS

| | | | |
|---|---|---|---|
| 1,667,802 | 5/1928 | Homan, Jr. | 33/178 B |
| 2,241,451 | 5/1941 | Fist | 128/2 S |
| 2,835,981 | 5/1958 | Kaufman | 33/174 N |
| 2,933,817 | 4/1960 | Puckett et al. | 33/178 B |
| 3,703,234 | 11/1972 | Howard | 33/178 B |
| 3,858,325 | 1/1975 | Goerler | 33/178 B |

FOREIGN PATENTS OR APPLICATIONS

| | | | |
|---|---|---|---|
| 569,995 | 1/1924 | France | 128/2 R |

*Primary Examiner*—William E. Kamm
*Attorney, Agent, or Firm*—Bill B. Berryhill

[57] ABSTRACT

A medical instrument for measuring tubular vessels and prosthetic grafts therefor comprising: a measuring ring of a diameter corresponding with the diameter of a selected prosthetic graft; an elongated rod attached to the ring; and a handle attached to the rod. The free end of the handle may be of a reduced lateral dimension corresponding with the limb diameter of a bifurcated prosthetic graft.

8 Claims, 4 Drawing Figures

TUBULAR MEASURING MEDICAL INSTRUMENTS

BACKGROUND OF THE INVENTION

1. Field of the Invention

The present invention pertains to medical instruments and devices. In particular, it pertains to measuring apparatus for determining the size of vessels and prosthetic grafts for the replacement of damaged or diseased vessel sections.

2. Description of the Prior Art

Frequently, in cardiovascular surgery, it is necessary to remove or bypass a section of a blood vessel for replacement or circumvention by a prosthetic graft. Depending on what section is removed or bypassed, the graft may be straight or bifurcated, having an aorta and, normally, two limbs. To determine the size graft needed for replacement, the vessel section being replaced or dissected should be measured, preferably before the vessel is severed or dissected. If this is not done, selection of the proper graft size may be by trial and error, consuming valuable surgery time. Furthermore, if the graft selected first is not the proper size, it becomes contaminated and must be resterilized before subsequent use. If contaminated by blood it must be discarded. Due to the materials therefor, grafts can only be resterilized a few times before they are permanently damaged and will have to be thrown away. Since they are expensive, this is a waste of money as well as time.

Quite frequently, grafts may be removed from their packages losing size identification. For this reason, a measuring device is also desirable to determine the graft size.

One problem associated with determining the size of a vessel, while still in the body, is the ability to measure within a body cavity. Sometimes these body cavities may be extremely deep, rendering certain types of instruments unusable.

There are few instruments available for measuring vessels and grafts. One which is available is of the caliper type, having a fixed point and a movable point on a movable caliper arm which, as the caliper arm moves, are positioned so that the points engage the vessel on opposite sides thereof. However, since vessels are generally very flexible, there is a distinct possibility that an inaccurate measurement may be taken by placing too much pressure on the caliper arm. In addition, vessels are not always disposed in the body for access by a caliper type device. An example of a caliper type measuring instrument may be seen in U.S. Pat. No. 3,740,779.

Some flat sheet type gauges have been used in the past for internal measurement of vessels and grafts. Of course, with such a measuring device, the vessel cannot be measured until it is severed from the body. As already pointed out, this may result in the loss of valuable surgical time. Furthermore, such a means of measuring a flexible vessel of graft can be improperly forced into the vessel or graft interior, causing the tubular structure to be elongated, accommodating the wrong size and maybe resulting in the selection of an improperly sized graft.

There is a long felt need for a suitable measuring instrument in cardiovascular surgery. The fact that none of those presently used has found wide acceptance, indicates that improvements in this area are awaited.

SUMMARY OF THE INVENTION

In the present invention, a set of instruments, one for each available graft size, is provided by which the vessel section to be replaced or bypassed can be measured before removal or dissection and by which unmarked grafts can be sized for resterilization and subsequent use. Thus, the handling and damaging of several very expensive grafts is prevented and unmarked grafts made available for reuse, saving money for both the hospital and the patient.

Each of the instruments comprises a measuring ring of a diameter corresponding with the diameter of a selected prosthetic graft of a particular size. The ring is attached to a handle by an intervening elongated rod. The elongated rod permits the instrument to be inserted, even into a deep body cavity, for measurement of a vessel or artery. The free end of the handle may be reduced in its lateral dimension to a size corresponding with the limb diameter of a bifurcated prosthetic graft whose aorta diameter corresponds with the diameter of the measuring ring.

The handle may be flat in construction so that several instruments, which make up a set, can be stored together in a compact space. The instruments of the set may be maintained as a unit by assembly with a retainer ring.

Since the instruments can be used to measure vessels before they are removed, valuable time can be saved. In addition, unmarked grafts may be measured for sterilization and reuse. In addition, the instruments prevent loss of time and waste of grafts inherent with trial and error methods. Many other objects and advantages of the invention will be apparent from the description which follows in conjunction with the accompanying drawings.

DESCRIPTION OF A PREFERRED EMBODIMENT

Figure 1:
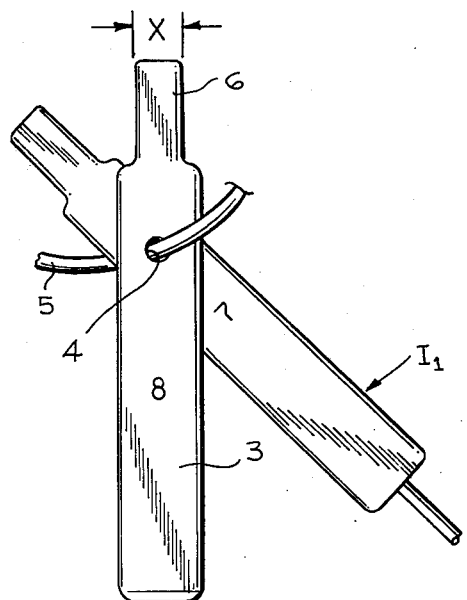
FIG. 1 is an elevation view of one instrument of a set, according to a preferred embodiment of the invention.

Referring first to FIG. 1, there is shown a measuring instrument I, according to a preferred embodiment of the invention. The instrument I may comprise one of a set of graduated instruments, instrument $I_1$ being illustrative of another of the set.

The instrument I comprises a measuring ring 1 attached to an elongated rod 2 which is attached at its other end to a handle 3. The measuring ring 1 is sized to correspond with the diameter of a preselected prosthetic vessel graft. The size may be marked on the handle 3 such as shown by the number "8" thereon. This would indicate that the size of the ring 1 and corresponding prosthetic graft is 8 millimeters.

The handle 3 is relatively thin and flat. This allows several instruments such as I and $I_1$ to be placed closely together for compact storage thereof. Each handle can be provided with an aperture 4 through which a retainer device, such as ring 5, may be passed to retain all instruments of the set together.

The free end 6 of the handle 3 may be reduced in dimension so that its lateral dimension X corresponds with the limb diameter of a bifurcated prosthetic graft whose aorta diameter corresponds with the diameter of ring 1. Generally, the limb diameter is one-half of the aorta diameter. However, this is not necessarily so and the dimension X would have to be sized for the particular type of grafts used.

The instrument I is preferably made of stainless steel or some other corrosion and contamination resistant material. Its construction lends itself to easy cleaning and sterilization.

Figure 2:
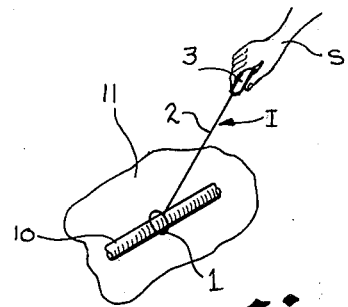
FIG. 2 is a pictorial view, illustrating the use of the invention in measuring a vessel within a body cavity during surgery.

Now referring to FIG. 2, the instrument I is shown in use for measuring a vessel 10 within a body cavity 11 during cardiovascular surgery. The handle 3 is grasped by the surgeon S and the ring 1 and rod 2 inserted into the body cavity so that the ring 1 lies adjacent the vessel to be replaced. The elongated rod permits the instrument to be used in very deep body cavities. By comparing the vessel to be replaced with the ring 1, a close estimate of its size can be determined. If the instrument I is not the proper size, the next graduated instrument is tried until the proper size is located. Then the surgeon can call for a prosthetic graft of a size corresponding with the vessel to be removed, actually before the vessel is severed.

Figure 3:
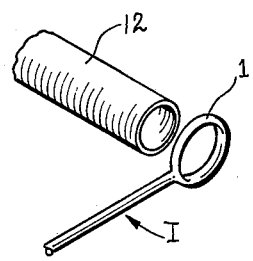
FIG. 3 is a pictorial view, illustrating use of the invention for measuring an unknown graft.

As sometimes occurs, when prosthetic grafts are removed from their packaging, their size becomes unknown. As illustrated in FIG. 3, the ring 1 of the instrument I can be held up next to the end of a prosthetic graft, such as the straight one 12 illustrated in FIG. 3 to determine its size.

Figure 4:
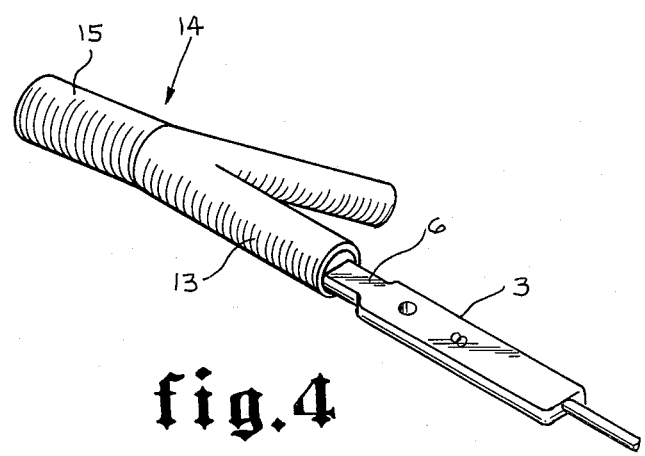
FIG. 4 is a pictorial view, illustrating use of the invention for measuring the limb of a bifurcated graft.

Occasionally, it may be necessary to measure the limb 13 of a bifurcated graft 14 rather than its aorta 15. (See FIG. 4) The instrument I is illustrated in FIG. 4 in this use. As shown, the free end 6 of the handle 3 is used for this purpose. The reduced dimension portion 6 is inserted into the interior of the limb for determining if these sizes correspond. If not, another instrument in the set is selected until the proper size is determined.

Thus, it can be seen that the instrument of the present invention is highly effective in determining vessel size before removal by surgery. In addition, it is useful in determining graft sizes, both straight grafts and bifurcated grafts. It is sturdily constructed, cheaply manufactured, easily operated, sanitary and reusable. It should find wide acceptance in the cardiovascular surgery field.

Although only one embodiment of the invention has been described herein, many variations thereof can be made by those skilled in the art without departing from the spirit of the invention. Therefore, it is intended that the scope of the invention be limited only by the claims which follow.

I claim:
1. A set of graduated medical instruments for measuring vessels and prosthetic grafts therefor, each of said instruments comprising:
   a handle member;
   an elongated rod member attached to said handle member; and
   a ring member attached to said rod member, said ring being of a diameter corresponding with the diameter of a selected one of said prosthetic vessel grafts.
2. A set of medical instruments as set forth in claim 1 in which the handle member of each of said instruments is flat having a thickness substantially less than its width so that said instruments may be closely positioned with each other for compact storage thereof.
3. A set of medical instruments as set forth in claim 2 in which the handle member of each of said instruments is provided with an aperture through which a keeper member is passed to maintain said instruments together as a set.
4. A set of medical instruments as set forth in claim 3 in which the width of the end of said handle member opposite said rod member is of a width corresponding with the diameter of the limb portions of a bifurcated prosthetic graft, the aorta diameter of which corresponds with the diameter of said instrument ring member.
5. A set of medical instruments as set forth in claim 1 in which the lateral dimension of the end of said handle member corresponds with the limb diameter of a bifurcated prosthetic graft, the aorta diameter of which corresponds with the diameter of said instrument ring member.
6. A set of medical instruments as set forth in claim 5 in which the lateral dimension of said handle member between said end and said rod member is greater than said end lateral dimension.
7. A medical instrument for measuring tubular vessels and prosthetic grafts therefor comprising:
   a measuring ring of a diameter corresponding with the diameter of a selected prosthetic vessel graft;
   an elongated rod attached to said ring; and
   a handle attached to said rod, the free end of said handle being of a reduced lateral dimension corresponding with the limb diameter of a bifurcated prosthetic graft, the aorta diameter of which corresponds with the diameter of said measuring ring.
8. A medical instrument as set forth in claim 7 in which said handle is flat, permitting a number of like instruments to be compactly stored together.

* * * * *